United States Patent [19]

Robinson

[11] 4,252,025

[45] Feb. 24, 1981

[54] ULTRASONIC DIAGNOSTIC APPARATUS

[75] Inventor: David E. Robinson, Bilgola Plateau, Australia

[73] Assignee: The Commonwealth of Australia, Phillip, Australia

[21] Appl. No.: 61,645

[22] Filed: Jul. 30, 1979

[30] Foreign Application Priority Data

Aug. 4, 1978 [AU] Australia .............................. PD5369

[51] Int. Cl.³ ............................................. G01N 29/00
[52] U.S. Cl. ....................................... 73/621; 73/626; 128/660
[58] Field of Search ................. 73/602, 620, 621, 625, 73/626; 128/660, 661

[56] References Cited

U.S. PATENT DOCUMENTS

| 4,074,564 | 2/1978 | Anderson | 73/602 X |
|---|---|---|---|
| 4,078,435 | 3/1978 | Kossoff et al. | 73/626 X |
| 4,137,775 | 2/1979 | LeMay | 73/626 X |

*Primary Examiner*—James J. Gill

[57] ABSTRACT

Apparatus for the ultrasonic examination of an object comprises:

means for transmitting pulses of ultrasonic energy along a plurality of beams into the object and receiving echoes of the pulses reflected along the beams by acoustic impedance discontinuities within the object, the means directing the beams from a plurality of spaced positions in a single plane relative to the object and along a plurality of beam directions in the single plane at each spaced position;

means for forming a first display of information representative of the position of acoustic impedance discontinuities within the object from the echoes received along the plurality of beams;

means for selecting a point or region within the object intersected by at least one beam direction from different ones of the spaced positions; and means for determining the shift of echoes from the selected point or region received along the beam in each beam direction caused by divergences of the velocity of propagation of ultrasonic energy through the object in the respective beam direction from a median value, and correlating the determinations of the shift of echoes in each beam direction to obtain information representative of the divergences of the velocity of propagation of ultrasonic energy from the median value within the object.

18 Claims, 4 Drawing Figures

ULTRASONIC DIAGNOSTIC APPARATUS

This invention relates to the technique of ultrasonic echoscopy of objects and in particular to means for decreasing the time required for examination of an object using the pulse-echo ultrasonic technique. It is particularly, but not solely, directed to the use of this technique in medical diagnostic examination.

Ultrasonic echoscopy provides information about an examined object which may be displayed in the form of an ultrasonic echogram. Such an echogram consists of a display of acoustic impedance discontinuities or reflecting surfaces in the object. It is obtained by directing a short pulse of ultrasonic energy, typically in the 1–30 MHz frequency range, into the examined object where any acoustic impedance discontinuities in the object reflect and return some of the energy in the form of an echo. This echo is received, converted into an electrical signal and displayed as an echogram on a cathode ray oscilloscope, a film, a chart or the like.

The echogram may constitute either a one dimensional or a two dimensional representation and in both cases the information is contained in the position and magnitude of the echo displayed. In a one dimensional display, the position along a base line is used to indicate the distance to the reflecting surface whilst the magnitude of the echo is displayed for example as a deflection of the base line or as an intensity change. In a two dimensional display, the position along a base line is used to indicate the distance to the reflecting surface as in a one dimensional display, and the direction of the base line is used to represent the direction of propagation of the acoustic energy. The two dimensional display is obtained by changing this direction of propagation of the acoustic energy and by instituting a similar but not necessarily identical movement of the base line of the display. The magnitude of the echo is displayed as for a one dimensional display, for example, as a deflection of the base line or as an intensity change.

The technique of ultrasonic echoscopy is used in medical diagnosis to obtain information about the anatomy of patients. The application of this technique is now widely investigated and is described, for example, by D. E. Robinson in Proceedings of the Institution of Radio and Electronics Engineers Australia, Vol. 31, No. 11, pages 385–392, November, 1970: "The Application of Ultrasound in Medical Diagnosis." As pointed out in this article ultrasonic echoscopy may be used to produce displays resembling anatomical cross-sections which have proved clinically useful when the desired information concerns physical dimensions, shapes of organs or structures or the like. Ultrasonic echography has proved of particular value as a diagnostic aid in the abdomen and pregnant uterus, eye, breast, lung, kidney, liver and heart, these being areas of soft tissue with little bone and air. In general, the technique is considered to complement other techniques to provide a more complete picture of the patient' condition, however, particularly in pregnancies, ultrasonic echoscopy may be useful in place of x-rays where the latter may not give sufficient information or may be dangerous. In medical use, a pulse of ultrasonic energy is transmitted into a patient in a known direction and echoes are received from reflecting surfaces within the body. The time delay between a transmitted pulse and the received echo depends on the distance from the transmitted to the reflecting surface and the distance information so obtained may be displayed in a suitable way for interpretation and clinical use as a one dimensional range reading or as a two dimensional cross section as previously described.

The two dimensional cross sectional display gives information only of the location and reflecting strength of ultrasound reflectors within the examined object. It is an object of this invention to provide an apparatus and method for providing additional information of the distribution of velocity of propagation within the examined object from the pulse echo data. Methods are known for utilising pulse echo data along single lines of sight or single directions to obtain average velocity information (Robinson U.S. Pat. No. 4,011,750, Australian Pat. No. 483477) using a single large aperture transducer with an annular array structure and signal processing means. This approach has the disadvantage that the single transducer system requires a large amount of time to form a compound scan echogram, due to mechanical limitations in the rate of movement and oscillation of the transducer in the water bath. The acquisition rate can be increased by the use of a plurality of transducers scanning in synchronism and an electronic switching system so that each transducer is activated in turn before the set of transducers is stepped to its next angular position, as taught by Kossoff in U.S. Pat. No. 3,939,696. Using this approach, it is not possible to use the velocity measurement taught by Robinson since the transducer size required by that method is too large and there is usually not sufficient room in the apparatus for the plurality of transducers required. It is an object of the present invention to overcome this difficulty by using the large aperture afforded by a combination of all transducers as taught by Kossoff in conjunction with a signal processing method to derive the required information.

The signal processing technique of reconstruction of cross sectional data from its projections is well known and is described, for example, in "Special Issue: Advances in Picture Reconstruction—Theory and Application" Vol. 6, No. 4 of Computers in Biology and Medicine, 1976. This technique has been applied in radio astronomy, electron microscopy, diagnostic radiology (known as computed axial tomography) and in a transmission method using ultrasonic sound waves. In the known ultrasound transmission method, the basic data recorded is the time taken for ultrasound to propagate between two transducers on opposite sides of an examined object such as the human body. The transducers are moved so that many measurements are made along many different lines and in many different directions. Since the time of flight, that is the time taken for propagation between the two transducers, is determined by the velocity of propagation within the examined object, it is possible using one of the well known computed tomography image reconstruction techniques to reconstruct a cross section of velocity distribution within the examined object. This technique, however, suffers the disadvantage that a complete transmission path through the object must be available, whereas in the human body this is not always so as large bony regions and gas filled organs are a barrier to ultrasound. As a result, the technique is only applicable to restricted areas in medical diagnostic examination.

It is an object of this invention to provide a method and means for obtaining velocity distribution information concerning an examined object by means of a reconstruction technique using pulse-echo input data.

This approach thus removes the need to achieve transmission through the object to be examined and as a result allow the examination of a larger variety of areas of the human body in medical diagnostic examination.

In a perfect pulse-echo imaging system operating in an examined object of constant velocity of propagation, the echoes from the same structures obtained along different lines of sight will exactly superimpose. In practice, however, due to variations in velocity of propagation within the examined object, the echoes are caused to be shifted along and across the line of sight due to refraction effects. In the known pulse-echo system, these shifts are aberrations of the system and cause a loss of resolution and a blurring of the image of the echogram. It is therefore an object of the present invention the isolate and interpret these shifts or aberrations so that they can be identified and removed, thus giving an improvement in resolution and clarity of the resulting image or echogram. It is a further object of the invention to use the shifts or aberrations as isolated and interpreted to provide additional information concerning the distribution of velocity of propagation within the examined object so that, for example in the case of medical diagnostic examination, information may be obtained from knowledge of this distribution of velocity of propagation. By analysing the differences in apparent position of echoes from the same structures when scanned from different directions, data equivalent to the time of flight or propagation of ultrasound between transducers at opposite sides of the body can be inferred. This data may then be subjected to the known procedures of computer tomography to obtain a cross sectional representation of velocity of propagation of ultrasound within the examined object. If desired, this information may then be displayed in conjunction with the B-Mode display by the methods taught by Kossoff and Robinson in Australian Pat. No. 490,105.

According to the present invention there is provided a method of ultrasonic examination of an object, which comprises the steps of:

transmitting pulses of ultrasonic energy along a plurality of beams into the said object and receiving echoes of said pulses reflected along said beams by acoustic impedance discontinuities within the object, said beams being directed from a plurality of spaced positions in a single plane relative to said object and along a plurality of beam directions in said single plane at each said spaced position; forming a first display of information representative of the position of acoustic impedance discontinuities within said object from said echoes received along said plurality of beams;

selecting a point or region within said object intersected by at least one beam direction from different ones of said spaced positions; and determining the shift or echoes from said selected point or region received along the beam in each said beam direction caused by divergences of the velocity of propagation of ultrasonic energy through said object in the respective beam direction from a median value, and correlating said determination of the shift of echoes in each said beam direction to obtain information representative of the divergences of the velocity of propagation of ultrasonic energy from said median value within said object.

In another aspect, there is provided apparatus for the ultrasonic examination of an object comprising:

means for transmitting pulses of ultrasonic energy along a plurality of beams into the said object and receiving echoes of said pulses reflected along said beams by acoustic impedance discontinuities within the object, said means directing said beams from a plurality of spaced positions in a single plane relative to said object and along a plurality of beam directions in said single plane at each said spaced position;

means for forming a first display of information representative of the position of acoustic impedance discontinuities within said object from said echoes received along said plurality of beams; means for selecting a point or region within said object intersected by at least one beam direction from different ones of said spaced positions; and means for determining the shift of echoes from said selected point or region received along the beam in each said beam direction caused by divergences of the velocity of propagation of ultrasonic energy through said object in the respective beam direction from a median value, and correlating said determinations of the shift of echoes in each said beam direction to obtain information representative of the divergences of the velocity of propagation of ultrasonic energy from said median value within said object.

The pulses may be transmitted and the echoes received by activation of a plurality of transducer means (for example, either single transducers or transducer arrays) each of the transducer means being positioned at one of the plurality of spaced positions. Alternatively, a single transducer means may be moved to each of the plurality of spaced positions during the examination of the object.

Further features of this invention will be apparent from the following description of one embodiment thereof, taken in conjunction with the accompanying drawings in which.

Figure 1:
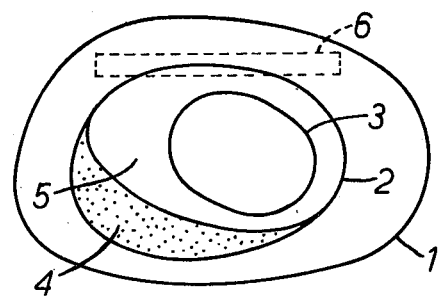
FIG. 1 represents a typical cross section of the pregnant uterus such as may be examined in an ultrasonic B-Mode examination.

In considering FIG. 1, the external outline of the patient's body 1 is displayed, together with its underlying fat and muscular tissue. The uterine wall 2 is usually seen and the baby's head or trunk 3 is represented as a circular structure with some internal echoes. The placenta 4 is seen as a speckled area applied to the uterine wall and the remainder of the uterine cavity 5 is seen as an echo-free area. The echoes from the posterior uterine wall 6 and associated structures may be used in the performance of the invention.

Figure 2:
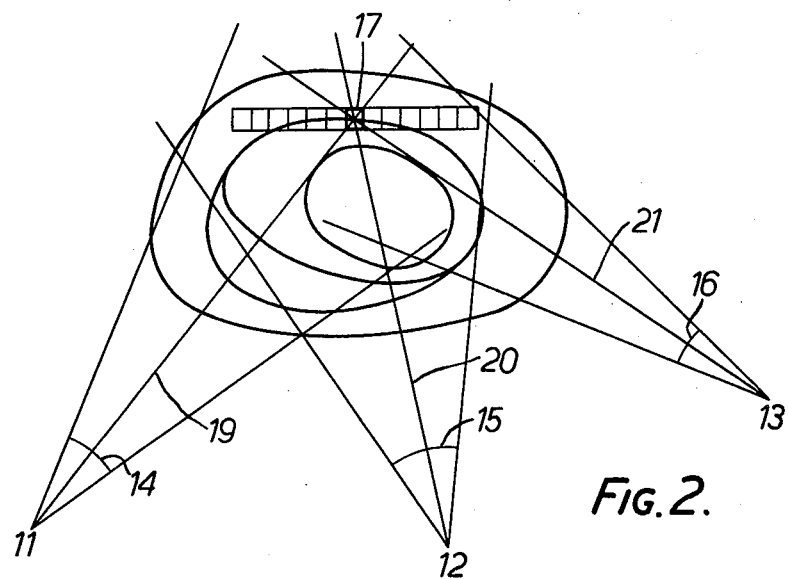
FIG. 2 illustrates by way of example the position of three transducers and their section geometry with respect to the cross section shown in FIG. 1.

Referring now to FIG. 2, there is shown by way of example the position of three transducers 11, 12, 13 and some typical ranges of angles of the lines of sight 14, 15, 16 therefrom with relationship to the scanned anatomy depicted in FIG. 1. In general, the method uses a plurality of transducers located at known positions in a single plane and adapted to scan in synchronism. It is known to form a cross-sectional sector scan B-Mode image from any single transducer or to form a compound scan B-Mode image from any combination of transducers. The images are all cross-sectional representations of the echo producing properties of the examined tissue, taken with different acoustic lines of sight. Further details concerning the mode of operation are, for example, disclosed in Kossoff U.S. Pat. No. 3,439,696. A particular region 17 within the scanned anatomy, preferably chosen by the operator to be behind all the structures whose velocity of propagation are to be determined (and which may, for example, be the posterior uterine wall 6 as shown in FIG. 1), is intersected by scan lines 19, 20, 21, one from each of transducers 11, 12 and 13 respectively. The position of echoes from region 17 on each of the separate sector scan images will be shifted along the respective beam axes by an amount depending on the variation in velocity of propagation along the respective beam axes 19, 20, 21. The amount of the shift along each beam axis from a median position can be regarded as a measure of the divergence of the velocity of propagation along the axis from its mean value. This procedure may be repeated for any number of regions adjacent to region 17 to obtain as many data points as are necessary to perform an image reconstruction by the procedure of one of the well known image reconstruction algorithms referred to previously. The reconstructed image represents a distribution of velocity variation from a median value, preferably but not restricted to that of water which is 1525 meters per second at 37° C.

A preferred method for deriving the shifts along the beam axis of the displayed echoes from their correct position is by the mathematical process of two dimensional cross correlation which is preferably carried out in a digital computer. This procedure compares two signals from different scan positions to determine the position at which the two signals most closely match one another. Another method of carrying out this process is by selection by the operator of highlight echoes which the operator has determined come from individual discrete reflectors. The apparent position of these echoes from different scan positions is then analysed by the computer to derive the shift in position.

Figure 3:
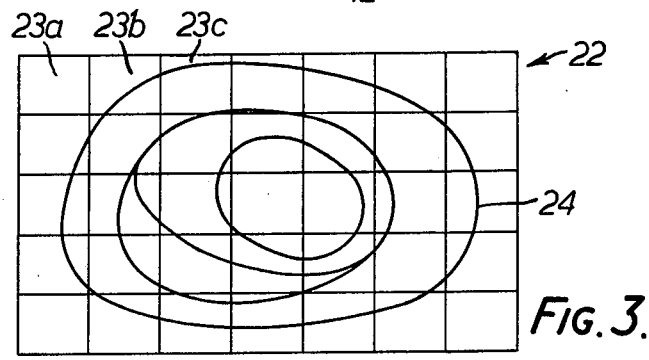
FIG. 3 represents a typical velocity determination with respect to the cross section shown in FIG. 1 derived with the use of the present invention.

FIG. 3 is a representation of the information available from the reconstruction algorithms. The spatial resolution of the velocity reconstruction is very much less than the spatial resolution of the originally derived pulse echo B-Mode representation of the cross-sectional anatomy. However, by displaying the velocity distribution on the B-Mode anatomical cross-section, for example as taught in Australian Pat. No. 490105, further information useful in clinical diagnosis is conveyed to the interpreter. Thus, in FIG. 3, a backround grid 22 is composed of typical resolution cells 23a, 23b, 23c..., by means of which appropriate velocity distribution determinations may be superimposed on the B-Mode anatomical cross-section 24. The velocity distribution appropriate to each cell may be displayed as described above to show, for example, in one cell a divergence of the velocity of propagation from a median value of −2%, and in an adjacent cell, a divergence of −4%.

Figure 4:
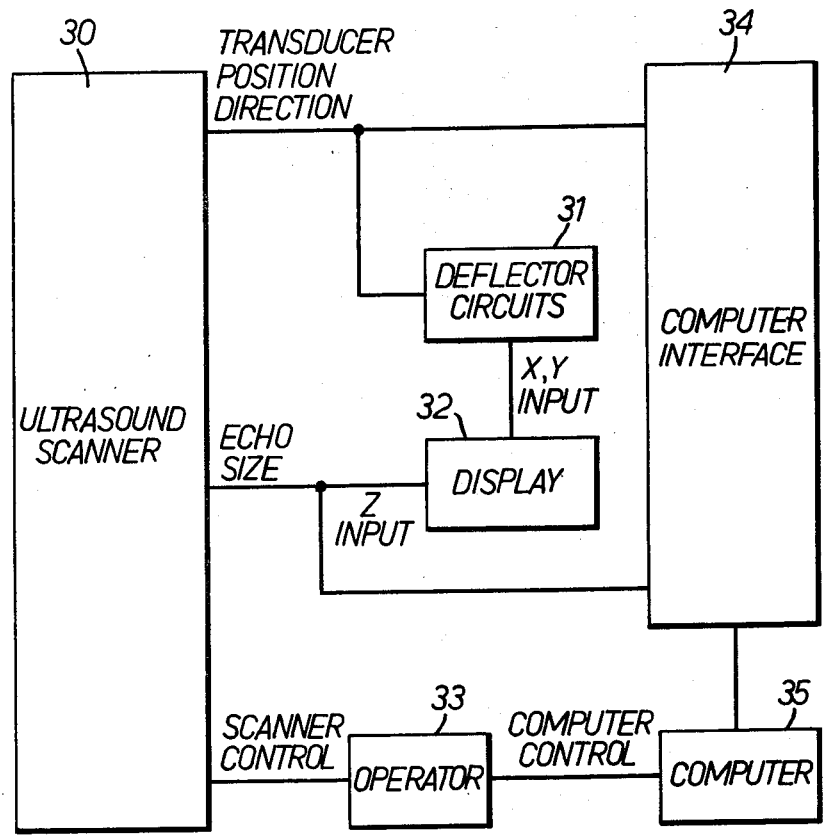
FIG. 4 is a block diagram of a typical apparatus required to perform the present invention.

FIG. 4 is a block diagram of the apparatus for performance of the present invention. The ultrasonic scanner 30, deflection circuits 31 and display 32 are well known in the art and reference may be made to Kossoff U.S. Pat. No. 3,939,696 for further details thereof. The scanner 30 provides means to determine the position and the orientation of the transducer lines of sight which are used in the deflection circuits 31 to provide x and y deflection voltages to the display 32. The echoes received by the transducers in the scanner 30 are amplified and processed before being applied to the X input of the display 32. The operator 33 controls the position of the scanner to fix the plane of cross section within the patient or other object under examination, and also controls the scanner imaging system to determine when a cross sectional image is to be obtained.

In addition to the known components herein before described, the apparatus shown in FIG. 4 includes a computer interface 34 which obtains signals from the scanner 30 representing transducer position and direction and echo size for transmission to the computer 35. The computer 35 then performs similar functions to the deflection circuits 31 and display 32 to provide within its memory a map of ultrasonic echoes in their appropriate positions within a scan plane. The operator 33 then selects a suitable region or set of regions (17 in FIG. 2) or suitable highlight echoes and the computer can then perform the required operations to determine the shifts along the lines of sight as taught by this invention. The reconstruction of a velocity distribution image as is well known in the art, or other further utilisation of the velocity distribution information as broadly described above, may then be carried out.

I claim:

1. A method of ultrasonic examination of an object, which comprises the steps of:
   transmitting pulses of ultrasonic energy along a plurality of beams into the said object and receiving echoes of said pulses reflected along said beams by acoustic impedance discontinuities within the object, said beams being directed from a plurality of spaced positions in a single plane relative to said object and along a plurality of beam directions in said single plane at each said spaced position;
   forming a first display of information representative of the position of acoustic impedance discontinuities within said object from said echoes received along said plurality of beams;
   selecting a point or region within said object intersected by at least one beam direction from different ones of said spaced positions; and
   determining the shift of echoes from said selected point or region received along the beam in each said beam direction caused by divergences of the velocity of propagation of ultrasonic energy through said object in the respective beam direction from a median value, and correlating said determinations of the shift of echoes in each said beam direction to obtain information representative of the divergences of the velocity of propagation of ultrasonic energy from said median value within said object.

2. A method according to claim 1, wherein a plurality of said points or regions within said object are selected, each of said points or regions being intersected by at least one beam direction from different ones of said spaced positions, and wherein said steps of determining the shift of echoes and correlating said determinations are carried out in respect of all of said selected points or regions.

3. A method according to claim 1, wherein said step of correlating said determinations of the shift of echoes includes the formation of a display of the distribution of said divergences of the velocity of propagation within said object.

4. A method according to claim 3, wherein said display of the distribution of said divergences of the velocity of propagation within said object is incorporated into said first display.

5. A method according to claim 3, wherein said display of the distribution of said diverences of the velocity of propagation within said object is formed as a second display of information.

6. A method according to claim 1, comprising the further step of utilising said information representative of the divergences of the velocity of propagation within said object in the formation of said first display of information to improve the resolution and clarity thereof.

7. A method according to claim 1, wherein said step of correlating said determinations of the shift of echoes in each said beam direction includes two-dimensional cross-correlation of said determinations.

8. A method according to claim 1, wherein said step of correlating said determinations of the shift of echoes in each said beam direction includes analysis of the apparent position of selected echoes from individual reflectors within the object.

9. A method according to claim 1, wherein said pulses are transmitted and said echoes are received along said plurality of beams by activation of a plurality of transducer means, each of said transducer means being positioned at one of said plurality of spaced positions.

10. A method according to claim 1, wherein said pulses are transmitted and said echoes are received along said plurality of beams by activation of a single transducer means, said transducer means being moved to each of said plurality of spaced positions during said examination of the object.

11. Apparatus for the ultrasonic examination of an object, comprising:
means for transmitting pulses of ultrasonic energy along a plurality of beams into the said object and receiving echoes of said pulses reflected along said beams by acoustic impedance discontinuities within the object, said means directing said beams from a plurality of spaced positions in a single plane relative to said object and along a plurality of beam directions in said single plane at each said spaced position;
means for forming a first display of information representative of the position of acoustic impedance discontinuities within said object from said echoes received along said plurality of beams;
means for selecting a point or region within said object intersected by at least one beam direction from different ones of said spaced positions; and
means for determining the shift of echoes from said selected point or region received along the beam in each said beam direction caused by divergences of the velocity of propagation of ultrasonic energy through said object in the respective beam direction from a median value, and correlating said determinations of the shift of echoes in each said beam direction to obtain information representative of the divergences of the velocity of propagation of ultrasonic energy from said median value within said object.

12. Apparatus according to claim 11, wherein said selecting means comprises means for selecting a plurality of points or regions within said object, each of said points or regions being intersected by at least one beam direction from different ones of said spaced positions, and wherein said determining and correlating means comprises means for determining the shift of echoes and correlating said determinations in respect of all said selected points or regions.

13. Apparatus according to claim 11, wherein said determining and correlating means comprises digital computing means.

14. Apparatus according to claim 11, wherein said determining and correlating means includes means for forming a display of the distribution of said divergences of the velocity of propagation within said object.

15. Apparatus according to claim 13, wherein said means for forming a display comprises means for incorporating a display of the distribution of said divergences of the velocity of propagation within said object into said first display.

16. Apparatus according to claim 11, wherein said determining and correlating means includes means for utilising said information representative of the divergences of the velocity of propagation within said object in the formation of said first display of information to improve the resolution and clarity thereof.

17. Apparatus according to claim 11, wherein said means for transmitting pulses and for receiving echoes comprises a plurality of transducer means, each of said transducer means being positioned at one of said plurality of spaced positions.

18. Apparatus according to claim 11, wherein said means for transmitting pulses and for receiving echoes comprises a single transducer means, said transducer means being moved to each of said plurality of spaced positions during said examination of the object.

* * * * *